(12) United States Patent
Kleiner et al.

(10) Patent No.: US 8,865,189 B2
(45) Date of Patent: Oct. 21, 2014

(54) POLY(ESTER AMIDE)-BASED DRUG DELIVERY SYSTEMS

(71) Applicant: Abbott Cardiovascular Systems Inc., Santa Clara, CA (US)

(72) Inventors: Lothar Walter Kleiner, Los Altos, CA (US); Jessica Reneé DesNoyer, Bedford, MA (US); Stephen Dirk Pacetti, San Jose, CA (US); Syed Faiyaz Ahmed Hossainy, Hayward, CA (US); O. Mikael Trollsas, San Jose, CA (US); Michael Huy Ngo, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 13/731,875

(22) Filed: Dec. 31, 2012

(65) Prior Publication Data
US 2013/0129794 A1 May 23, 2013

Related U.S. Application Data

(60) Continuation of application No. 13/037,166, filed on Feb. 28, 2011, now Pat. No. 8,377,499, and a division of application No. 11/365,549, filed on Feb. 28, 2006, now Pat. No. 7,910,152.

(51) Int. Cl.
*A61L 27/34* (2006.01)
*A61L 31/10* (2006.01)
*A61L 31/16* (2006.01)

(52) U.S. Cl.
CPC ........... *A61L 27/34* (2013.01); *A61L 2300/606* (2013.01); *A61L 2300/416* (2013.01); *A61L 31/10* (2013.01); *A61L 2300/602* (2013.01); *A61L 31/16* (2013.01)
USPC ........................... 424/400; 514/291; 514/449

(58) Field of Classification Search
None
See application file for complete search history.

(56) References Cited

U.S. PATENT DOCUMENTS

| 4,304,767 A | 12/1981 | Heller et al. |
|---|---|---|
| 4,368,090 A | 1/1983 | Mumcu et al. |
| 4,483,975 A | 11/1984 | De Jong et al. |
| 4,800,882 A | 1/1989 | Gianturco |
| 4,886,062 A | 12/1989 | Wiktor |
| 5,124,219 A | 6/1992 | Shintani et al. |
| 4,733,665 B1 | 1/1994 | Palmaz |
| 5,489,667 A | 2/1996 | Knipf et al. |
| 5,509,899 A | 4/1996 | Fan et al. |
| 5,581,387 A | 12/1996 | Cahill |
| 5,644,020 A | 7/1997 | Timmermann et al. |
| 5,861,387 A | 1/1999 | Labrie et al. |
| 5,880,220 A | 3/1999 | Warzelhan et al. |
| 5,977,163 A | 11/1999 | Li et al. |
| 6,153,252 A | 11/2000 | Hossainy et al. |
| 6,277,927 B1 | 8/2001 | Roby et al. |
| 6,316,585 B1 | 11/2001 | Lele et al. |
| 6,420,045 B1 | 7/2002 | Faulhammer et al. |
| 6,451,373 B1 | 9/2002 | Hossainy et al. |
| 6,503,538 B1 | 1/2003 | Chu et al. |
| 6,600,010 B2 | 7/2003 | Mao et al. |
| 6,660,034 B1 | 12/2003 | Madrusov et al. |
| 6,703,040 B2 | 3/2004 | Katsarava et al. |
| 6,838,493 B2 | 1/2005 | Williams et al. |
| 7,056,591 B1 | 6/2006 | Pacetti et al. |
| 7,063,884 B2 | 6/2006 | Hossainy et al. |
| 7,077,859 B2 | 7/2006 | Sirhan et al. |
| 7,141,061 B2 | 11/2006 | Williams et al. |
| 7,166,680 B2 | 1/2007 | DesNoyer et al. |
| 7,202,325 B2 | 4/2007 | Hossainy et al. |
| 7,220,816 B2 | 5/2007 | Pacetti et al. |
| 7,390,497 B2 | 6/2008 | DesNoyer et al. |
| 7,419,504 B2 | 9/2008 | Hossainy |
| 7,435,788 B2 | 10/2008 | Pacetti et al. |
| 7,445,792 B2 | 11/2008 | Toner et al. |
| 7,691,401 B2 | 4/2010 | Castro et al. |
| 7,731,987 B2 | 6/2010 | DesNoyer et al. |
| 7,807,211 B2 | 10/2010 | Hossainy et al. |
| 7,820,732 B2 | 10/2010 | Hossainy et al. |
| 7,910,152 B2 | 3/2011 | Kleiner et al. |
| 8,007,775 B2 | 8/2011 | Hossainy et al. |
| 8,021,678 B2 | 9/2011 | Hossainy et al. |
| 8,030,436 B2 | 10/2011 | Pacetti et al. |
| 8,034,364 B2 | 10/2011 | DesNoyer et al. |
| 8,048,442 B1 | 11/2011 | Hossainy et al. |
| 8,088,404 B2 | 1/2012 | Udipi et al. |
| 8,192,752 B2 | 6/2012 | Tang et al. |
| 8,246,973 B2 | 8/2012 | Hossainy et al. |

(Continued)

FOREIGN PATENT DOCUMENTS

EP 0 583 888 2/1994
EP 0 778 250 6/1997

(Continued)

OTHER PUBLICATIONS

U.S. Appl. No. 10/816,072, filed Mar. 31, 2004, Dugan et al.
International Search Report for PCT/US2007/002398 filed Jan. 29, 2007, mailed Mar. 29, 2008, 18 pgs.
International Search Report for PCT/US2005/017690 filed May 18, 2005, mailed Dec. 1, 2005, 7 pgs.
International Search Report for PCT/US2007/013327, filed May 6, 2007, mailed Nov. 30, 2007, 4 pgs.
International Search Report for PCT/US2007/015902, filed Jul. 12, 2007, mailed Nov. 30, 2007, 3 pgs.
"DOW Oxygenated Solvents—UNOXOL™ Diol-The New Building Block for Coatings", Dow Chem. Co. Product Information (2011) 1 pg.
Blindt et al. "A Novel Drug-Eluting Stent Coated With an Integrin-Binding Cyclic Arg-Gly-Asp Peptide Inhibits Neointimal Hyperplasia by Recruiting Endothelial Progenitor Cells", J. of Am. College of Cardiology vol. 47, No. 9, pp. 1786-1795 (2006).

(Continued)

*Primary Examiner* — Robert A Wax
*Assistant Examiner* — Randeep Singh
(74) *Attorney, Agent, or Firm* — Squire Patton Boggs (US) LLP

(57) ABSTRACT

Implantable medical devices including a coating having a bioactive agent and a poly(ester amide) polymer. Methods of forming these coatings are also described.

7 Claims, 1 Drawing Sheet

(56) References Cited

U.S. PATENT DOCUMENTS

| | | | |
|---|---|---|---|
| 8,309,112 | B2 | 11/2012 | Glauser et al. |
| 8,323,676 | B2 | 12/2012 | Lim et al. |
| 2002/0015720 | A1* | 2/2002 | Katsarava et al. ............ 424/426 |
| 2003/0050692 | A1* | 3/2003 | Sirhan et al. ................. 623/1.42 |
| 2004/0034409 | A1 | 2/2004 | Heublein et al. |
| 2004/0072857 | A1 | 4/2004 | Waugh et al. |
| 2004/0073297 | A1 | 4/2004 | Rhode et al. |
| 2004/0126405 | A1 | 7/2004 | Sahatjian et al. |
| 2004/0170685 | A1 | 9/2004 | Carpenter et al. |
| 2004/0185081 | A1 | 9/2004 | Verlee et al. |
| 2005/0002983 | A1* | 1/2005 | Johnson, Jr. ................. 424/423 |
| 2005/0008671 | A1 | 1/2005 | Van Antwerp |
| 2005/0055075 | A1 | 3/2005 | Pinchuk et al. |
| 2005/0106204 | A1 | 5/2005 | Hossainy et al. |
| 2005/0125054 | A1* | 6/2005 | Bhat et al. ................... 623/1.42 |
| 2005/0131201 | A1* | 6/2005 | Pacetti et al. ................ 528/272 |
| 2005/0137715 | A1 | 6/2005 | Phan et al. |
| 2005/0208091 | A1 | 9/2005 | Pacetti |
| 2005/0265960 | A1 | 12/2005 | Pacetti et al. |
| 2005/0266038 | A1 | 12/2005 | Glauser et al. |
| 2005/0271700 | A1 | 12/2005 | DesNoyer et al. |
| 2005/0283229 | A1 | 12/2005 | Dugan et al. |
| 2005/0288481 | A1 | 12/2005 | DesNoyer et al. |
| 2006/0089485 | A1 | 4/2006 | DesNoyer et al. |
| 2006/0115513 | A1 | 6/2006 | Hossainy |
| 2007/0134288 | A1 | 6/2007 | Parsonage et al. |
| 2007/0280988 | A1 | 12/2007 | Ludwig et al. |
| 2007/0280991 | A1 | 12/2007 | Glauser et al. |
| 2008/0014245 | A1 | 1/2008 | Pacetti et al. |
| 2008/0124372 | A1 | 5/2008 | Hossainy et al. |
| 2009/0258028 | A1 | 10/2009 | Glauser et al. |
| 2009/0324671 | A1 | 12/2009 | Ngo et al. |
| 2010/0047319 | A1 | 2/2010 | Ngo et al. |
| 2011/0086162 | A1 | 4/2011 | Hossainy et al. |
| 2011/0153004 | A1 | 6/2011 | Kleiner et al. |
| 2011/0200660 | A1 | 8/2011 | Kleiner et al. |

FOREIGN PATENT DOCUMENTS

| | | |
|---|---|---|
| EP | 1 795 185 | 6/2007 |
| GB | 1 137 209 | 12/1968 |
| WO | WO 98/32777 | 7/1998 |
| WO | WO 00/56376 | 9/2000 |
| WO | WO 02/18477 | 3/2002 |
| WO | WO 2004/014449 | 2/2004 |
| WO | WO 2004/022119 | 3/2004 |
| WO | WO 2004/060428 | 7/2004 |
| WO | WO 2005/011770 | 2/2005 |
| WO | WO 2005/039489 | 5/2005 |
| WO | WO 2005/042600 | 5/2005 |
| WO | WO 2005/051445 | 6/2005 |
| WO | WO 2005/061024 | 7/2005 |
| WO | WO 2005/066241 | 7/2005 |
| WO | WO 2005/089824 | 9/2005 |
| WO | WO 2005/092406 | 10/2005 |
| WO | WO 2005/121250 | 12/2005 |
| WO | WO 2006/112932 | 10/2006 |
| WO | WO 2007/123872 | 11/2007 |
| WO | WO 2010/002584 | 1/2010 |

OTHER PUBLICATIONS

Fitzgerald et al. "Investigation of the mechanisms governing the release of levamisole from poly-lactide-co-glycolide delivery systems", Journal of Controlled Release 42: pp. 125-132 (1996).

Frank et al. "Controlled release from bioerodible polymers: effect of drug type and polymer composition", Journal of Controlled Release 102 pp. 333-344 (2005).

Huang et al., "Biodegradable Polymers Derived from Aminoacids", Macromol. Symp. 144, pp. 7-32 (1999).

Katsarava et al., Amino Acid-Based Bioanalogous Polymers. Synthesis and Study of Regular Polyester amide)s Based on Bis(a-amino acid)a,co-Alkylene Diesters and Aliphatic Dicarboxylic Acids, Journal of Polymer Science, Part A: Polymer Chemistry, 37(4), 391-407 (1999).

Middleton et al., "Synthetic biodegradable polymers as orthopedic devices", Biomaterials, vol. 21, pp. 2335-2346 (2000).

Roesler et al. Tris-3-(1-aziridino) propionates and their use in formulated products, Prog. Organic Coatings 50(1), pp. 1-27 (2004).

Saotome, et al., "Novel Enzymatically Degradable Polymers Comprising α-Amino Acid, 1,2-Ethanediol,and Adipic Acid", Chemistry Letters, pp. 21-24 (1991).

SIGMA-ALDRICH product information for Paclitaxel, 3pgs (2009).

International Search Rep. for PCT/US2007/002398 filed Jan. 29, 2007, mailed Apr. 29, 2008, 18 pgs.

Chandrasekar et al., *Coronary Artery Endothelial Protection After Local Delivery of 17β-Estradiol During Balloon Angioplasty in a Porcine Model: A Potential New Pharmacologic Approach to Improve Endothelial Function*, J. of Am. College of Cardiology, vol. 38, No. 5, pp. 1570-1576 (2001).

De Lezo et al., *Intracoronary Ultrasound Assessment of Directional Coronary Atherectomy: Immediate and Follow-Up Findings*, JACC vol. 21, No. 2, pp. 298-307 (1993).

Moreno et al., *Macrophage Infiltration Predicts Restenosis After Coronary Intervention in Patients with Unstable Angina*, Circulation, vol. 94, No. 12, pp, 3098-3102 (1996).

Oikawa et al., *Mechanisms of Acute Gain and Late Lumen Loss After Atherectomy in Different Preintervention Arterial Remodeling Patterns*, The Am. J. of Cardiology, vol. 89, pp. 505-510 (2002).

Park et al., "Membrane formation by water vapor incuded phase inversion", J. of Membrane Science 156 pp. 169-178 (1999).

Scully et al., *Effect of a heparan sulphate with high affinity for antithrombin III upon inactivation of thrombin and coagulaton Factor Xa*, Biochem J. 262, pp. 651-658 (1989).

Virmani et al., *Lessons From Sudden Coronary Death a Comprehensive Morphological Classification Scheme for Atherosclerotic Lesions*, Arterioscler Thromb Vasc Biol. pp. 1262-1275 (2000).

* cited by examiner

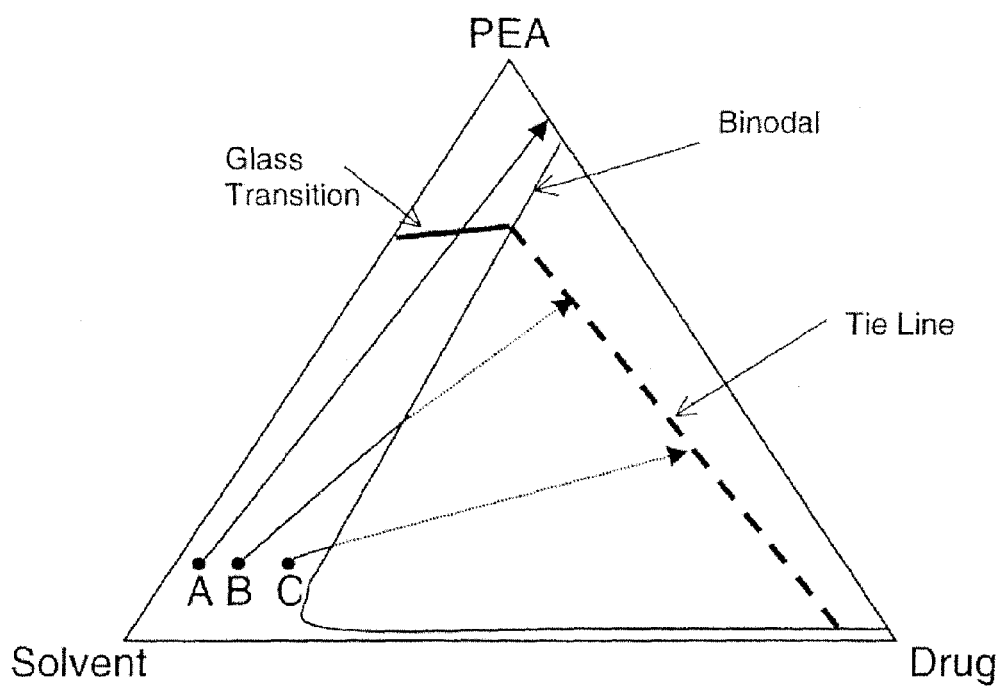

POLY(ESTER AMIDE)-BASED DRUG DELIVERY SYSTEMS

CROSS-REFERENCE TO RELATED APPLICATIONS

This application is a continuation of U.S. application Ser. No. 13/037,166, filed on Feb. 28, 2011, which is a divisional application of U.S. application Ser. No. 11/365,549, filed on Feb. 28, 2006, and both of these applications are incorporated by reference in their entirety, including any drawings, herein, application Ser. No. 11/365,549 issued as U.S. Pat. No. 7,910,152 on Mar. 22, 2011. Application Ser. No. 13/037,166 published as U.S. Patent Application Publication No. US 2011-0151104 A1 on Jun. 23, 2011 and issued as U.S. Pat. No. 8,377,499 on Feb. 19 2013.

FIELD OF THE INVENTION

This invention is generally related to poly(ester amide)-based drug delivery systems.

DESCRIPTION OF THE STATE OF THE ART

Stents play an important role in a variety of medical procedures, for example, percutaneous transluminal coronary angioplasty (PTCA), which is a procedure used to treat heart disease. In PTCA, a balloon catheter is inserted through a brachial or femoral artery, positioned across a coronary artery occlusion, inflated to compress atherosclerotic plaque and open the lumen of the coronary artery, deflated and withdrawn. Problems with PTCA include formation of intimal flaps or torn arterial linings, both of which can create another occlusion in the lumen of the coronary artery. Moreover, thrombosis and restenosis may occur several months after the procedure and require additional angioplasty or a surgical by-pass operation. Agent-coated stents have caused dramatic reductions in stent restenosis rates by inhibiting the tissue growth associated with restenosis. Stents are generally implanted to reduce occlusions, inhibit thrombosis and restenosis, and maintain patency within vascular lumens, for example, the lumen of a coronary artery.

Stents are also being developed to provide for a means of local delivery of agents. Local delivery of agents is often preferred over systemic delivery, particularly where high systemic doses are necessary to treat a site within a subject, but where high systemic doses create adverse effects. Proposed local delivery methods include coating the medical article surface with a polymeric carrier and attaching an agent to or blending it with the carrier.

For example, one method of applying multiple agents involves blending the agents together in one formulation, such as in a polymer matrix, and applying the blend to the stent surface. A disadvantage of this method is that the polymeric matrix morphology (arrangement of molecules in the matrix) causes the agents to release somewhat variably from the matrix causing the agents to compete with one another for release. In such a blend, controlling the release of the individual agents is challenging and can be considered unpredictable.

Controlling the performance of medical articles, for example, controlling the release of drugs, is an important aspect in medical device design. In addition to improving the bioactive, biobeneficial, or diagnostic results from administering agents, control over the release rate is important in designing and maintaining the physical and mechanical properties of medical devices and coatings, as well, and perhaps allows for the use of more desirable polymeric matrix components.

Currently, polymeric compositions frequently produce material that fails to meet desired performance characteristics. The most straightforward way of selecting polymer components such that the mixture or composition meets the desired characteristics is to choose the components based on their individual characteristics. Unfortunately, the combinations do not always exhibit a combination of the characteristics present in the individual components. Polymer characteristics vary from polymer to polymer based on a host of factors that can depend on the chain-to-chain interaction in the polymer or the arrangement of functional groups at the polymer's surface, among other factors. But when one polymer is combined with another, some of the factors are no longer present. Using the examples above, the chain-to-chain interaction in a polymer combination can differ because the types of chains differ. Similarly, the arrangement of functional groups at the surface can be different because the mixture contains a different cohort of surface groups. Because factors influencing polymer characteristics change upon combination with other polymers, components that individually have desired characteristics do not always yield a combination that adequately meets some desired set of performance characteristics. Furthermore, medical articles change morphologically during processing and storage, as well as after application in vivo. Unfortunately, the predictability, and consequently the clinical utility, of a medical article can rely on the ability to control these changes.

Accordingly, there is a need for control over the morphology of a polymeric matrix. The following embodiments address the above-identified problems and needs.

SUMMARY

The present invention provides a method for forming a coating having a controlled morphology for controlling the release of an agent from the coating. In some embodiments, the method includes:

providing a coating composition comprising a polymer and a polymer solvent, applying the coating composition onto the medical device, inducing a phase inversion process in the composition, thereby causing the composition to form a layer or coating on the medical device.

The coating composition can include a non-solvent of the polymer. The non-solvent of the polymer can also be a bioactive agent. Some examples of the agent can be paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), pimecrolimus, imatinib mesylate, midostaurin, clobetasol, bioactive RGD, CD-34 antibody, abciximab (ReoPro™), progenitor cell capturing antibody, prohealing drugs, prodrugs thereof, co-drugs thereof, or a combination thereof.

A medical device having a coating described herein can be used to treat, prevent, or ameliorate a vascular medical condition. Some exemplary vascular medical conditions include atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

BRIEF DESCRIPTION OF THE DRAWING

FIG. 1 is a ternary phase diagram of a poly(ester amide)/drug/solvent solution.

DETAILED DESCRIPTION

The present invention provides a method for forming a coating having a controlled morphology for controlling the release of an agent from the coating. In some embodiments, the method includes:

providing a coating composition comprising a polymer and a polymer solvent, applying the coating composition onto the medical device to form a layer of the composition on the medical device, inducing a phase inversion process in the layer, thereby causing the layer to form the coating on the medical device.

The coating composition can include a non-solvent of the polymer. The non-solvent of the polymer can also be a bioactive agent such as a drug. Some examples of the agent can be paclitaxel, docetaxel, estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), pimecrolimus, imatinib mesylate, midostaurin, clobetasol, bioactive RGD, CD-34 antibody, abciximab (REOPRO), progenitor cell capturing antibody, prohealing drugs, prodrugs thereof, co-drugs thereof, or a combination thereof. In some embodiments, the agent or drug can be soluble in the polymer matrix of the coating.

A medical device having a coating described herein can be used to treat, prevent, or ameliorate a vascular medical condition. Some exemplary vascular medical conditions include atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

Phase Inversion

Phase inversion is a process in which, for example, a concentrated polymer solution is converted into a solid network (e.g., a solid gel network) with desirable properties. In a phase inversion process, a polymer solution can be quenched to, for example, a region in its phase diagram (see FIG. 1) where the polymer can phase separate into a polymer-rich phase (e.g., a continuous polymer-rich phase) that surrounds a dispersed non-solvent-rich phase. The quench can be achieved by several mechanisms. For example, a non-solvent can trigger the phase inversion in a coating. Some other examples of means to induce the phase inversion in a coating include, but are not limited to, lyophilization of the solvent or extracting the solvent from the polymer by using a non-solvent where the non-solvent and solvent can be mutually miscible. In some embodiments, phase inversion can be induced by other means including, e.g., supercritical fluid extraction of the solvent from the polymer, removing the solvent by freeze drying, removing the solvent by heating under vacuum, or removing the solvent by vacuum at room temperature.

In some embodiments utilizing a single solvent system, a quench mechanism can be a temperature change, such as freezing or evaporation of the solvent. For a multiple solvent system, having a solvent and at least a non-solvent where the non-solvent has a higher boiling point than the solvent, evaporating the solvent and allowing the non-solvent to remain in the system can induce phase inversion. In some embodiments, a quench mechanism can be condensation or absorption of water into a coating during the coating process (e.g., in the coating step or drying step). Water can be a non-solvent of a polymer such as poly(ester amide) (PEA) and thus can trigger phase inversion in a coating that includes the polymer.

In some embodiments, in a phase inversion process, polymer solutions can be dilute.

In various embodiments, a phase inversion process can convert a polymer solution into a polymer membrane with or without residual solvent, and with or without dissolved or phase separated agents or drugs. IN some embodiments, agents or drugs are referred to as non-solvents.

In some embodiments, the quench is thermally induced to cause phase inversion. For example, the processes of spray coating and subsequent drying can cause rapid evaporation of a solvent, which cools the coating, resulting in a thermally induced phase transition (phase inversion). In some embodiments, phase inversion in the coating can be induced with a cold stream of gas or induced in a cold environment.

As used herein, the term "solvent" refers to a solvent of a polymer in a coating (e.g., a poly(ester amide) (PEA)). Solvents for a coating polymer include, but are not limited to, for example, $CH_2Cl_2$, chloroform, ethanol, isopropanol, n-propanol, dimethylformamide, dimethylacetamide, dimethylsulfoxide. In some embodiments, the solvent can be alcohols (e.g., methanol, ethanol, 1,3-propanol, 1,4-butanol), heptane, hexane, pentane, cyclohexanone, trichloroethane, acetone, tetrahydrofuran (THF), dimethyl acetamide (DMAc), dioxane, toluene, xylene, dimethyl sulfoxide (DMSO), dimethyl formamide (DMF), ethyl acetate, methyl ethyl ketone (MEK), and acetonitrile.

The term "non-solvent" refers to a non-solvent of a polymer in a coating (e.g., a poly(ester amide) (PEA)). Solvents and non-solvents are polymer dependent. Therefore, non-solvents for a coating polymer can include any of the solvent described above. Some examples of non-solvents include, but are not limited to, water, dioxane, acetone, toluene, cyclohexanone, methylethyl ketone, benzene, toluene, xylene, pentane, hexane, cyclohexane, octane, or a drug such as everolimus.

Table 1 summarizes some examples of solvents or non-solvents of a polymer.

TABLE 1

| PEA Polymer | Solvent | Non-solvent |
| --- | --- | --- |
| PEA-TEMPO, PEA-Benzyl | Methanol, Ethanol, n-Propanol, Isopropanol, 1-Butanol, DMAC, THF, DMF, Dichloromethane, DMSO, Chloroform, Trichloroethane, | Water, Dioxane, Cyclohexanone, MEK, Benzene, Toluene, Xylene, Pentane, Hexane, Heptane, Octane, Cyclohexane, and Acetone |

TABLE 1-continued

| PEA Polymer | Solvent | Non-solvent |
|---|---|---|
| 0.5 L-Leucine (cyclohexanediol)<br>0.5 L-Leucine (hexanediol) sebacinate<br>See [A] | Tetrachloroethane, and Trichloroethylene<br>Methanol, Ethanol, n-Propanol, Isopropanol, 1-Butanol, DMAC, THF, DMF, Dichloromethane, DMSO, Chloroform, Trichloroethane, Tetrachloroethane, and Trichloroethylene | Water, Dioxane, Cyclohexanone, MEK, Benzene, Toluene, Xylene, Pentane, Hexane, Heptane, Octane, Cyclohexane, and Acetone |
| L-Phenyl Alanine (propanediol) sebacinate<br>See [B] | DMAC, THF, DMF, Dichloromethane, DMSO, Chloroform, Trichloroethane, Tetrachloroethane, and Trichloroethylene | Water, Dioxane, Cyclohexanone, MEK, Benzene, Toluene, Xylene, Pentane, Hexane, Heptane, Octane, Cyclohexane, Acetone, Methanol, Ethanol, n-Propanol, Isopropanol, and 1-Butanol |

[A]
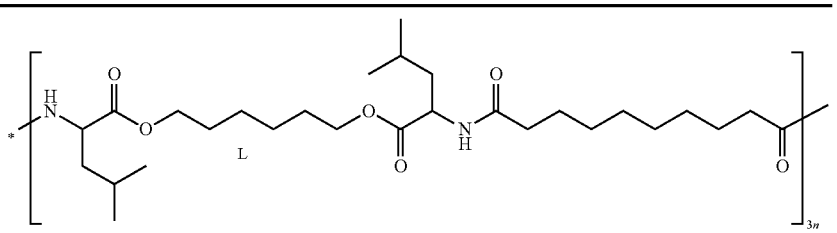

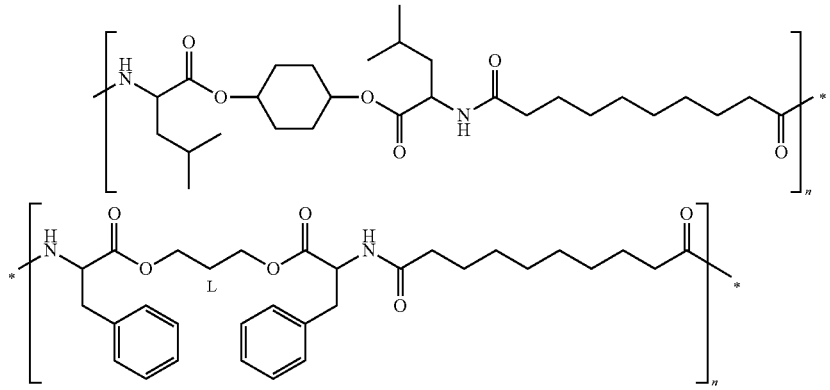

[B]

The polymer in the coating that can be subjected to a phase inversion process can be any biocompatible polymer. In general, the polymer preferably has a glass transition temperature ($T_g$) about or above ambient temperature because the operational temperature for a medical device is generally ambient temperature or body temperature and, if a polymer has a $T_g$ below ambient temperature, a solidification mechanism will not be in place for the polymer in a coating at the operational temperature of the medical device. Further, a preferred polymer or polymeric material preferably has a $T_g$ above about body temperature (e.g., 37° C.) so that the coating structure will not be lost upon implantation of the medical device (e.g., a stent). However, in some embodiments, a polymer can have a $T_g$ lower than ambient temperature and be included in a polymer solution subjected to the phase inversion process described herein. In these embodiments, the polymer solution should have one or more components having a $T_g$ above about ambient or body temperature.

A coating formed from a phase inversion process can have a variety of morphologies. Some exemplary forms of morphology include, but are not limited to, interconnected non-solvent rich phase, isolated non-solvent-rich phase, and sometimes, a morphology substantially free from the non-solvent-rich phase, depending on the total volume of the phase and the rate at which phase inversion occurs. In some embodiments, the coating morphology can have a two-phase structure having pores and/or channels. A newly formed two-phase structure can undergo a brief period of pore growth or coarsening to minimize its total interfacial free energy. The coarsening period can continue until a solidification mechanism (e.g., glass transition, crystallization) decreases the system mobility to an extent that all pore or channel growth ceases and the final morphology essentially is frozen into place.

The coating morphology can be tailored by controlling the phase inversion process by varying processing conditions. Such processing conditions can be, for example, selection of solvents, non-solvents, or polymers for forming the coating, evaporation rate of solvent, processing temperature, ambient humidity, or pressure.

In some embodiments, a coating composition system that includes a PEA polymer, a solvent and a drug can be used to form a coating. Such a coating composition system can have a ternary phase diagram as shown in FIG. 1. Some exemplary PEA polymers include three building blocks: an amino acid, a diol, and a diacid. The diacid can be, for example, a C2 to C12 diacid (e.g., aliphatic diacid with or without unsaturation or aromatic diacid). The diol can be, for example, a C2 to C12 diol, which can be a straight diol or branch diol with or without unsaturation. The amino acid can be, for example, glycine, valine, alanine, leucine, isoleucine, and/or phenyl alanine. An optional second amino acid can be included, which could include lysine, tyrosine, glutamic acid, or cysteine. The second amino acid can also contain a side group for attaching to a bioactive agent (e.g., pharmacologically active compound(s)) or property modifier(s). Some exemplary methods of making PEA are described in U.S. Pat. No. 6,503,538 B1. In some embodiments, the PEA polymer can be synthesized according to Scheme I:

membrane structure into place. Composition B is expected to have a lower fraction of the dispersed drug-rich phase than composition C. The drug-release rate will increase as the fraction of the dispersed drug-rich phase increases.

In some embodiments, a coating composition system can have a drug, solvent, non-solvent, and a PEA polymer. Such a quaternary system can have a phase diagram that one of ordinary skill in the art can readily understand.

PEA formulations based on different solvents or different drugs can have different phase diagrams and different phase inversion dynamics, which allow the design of systems with

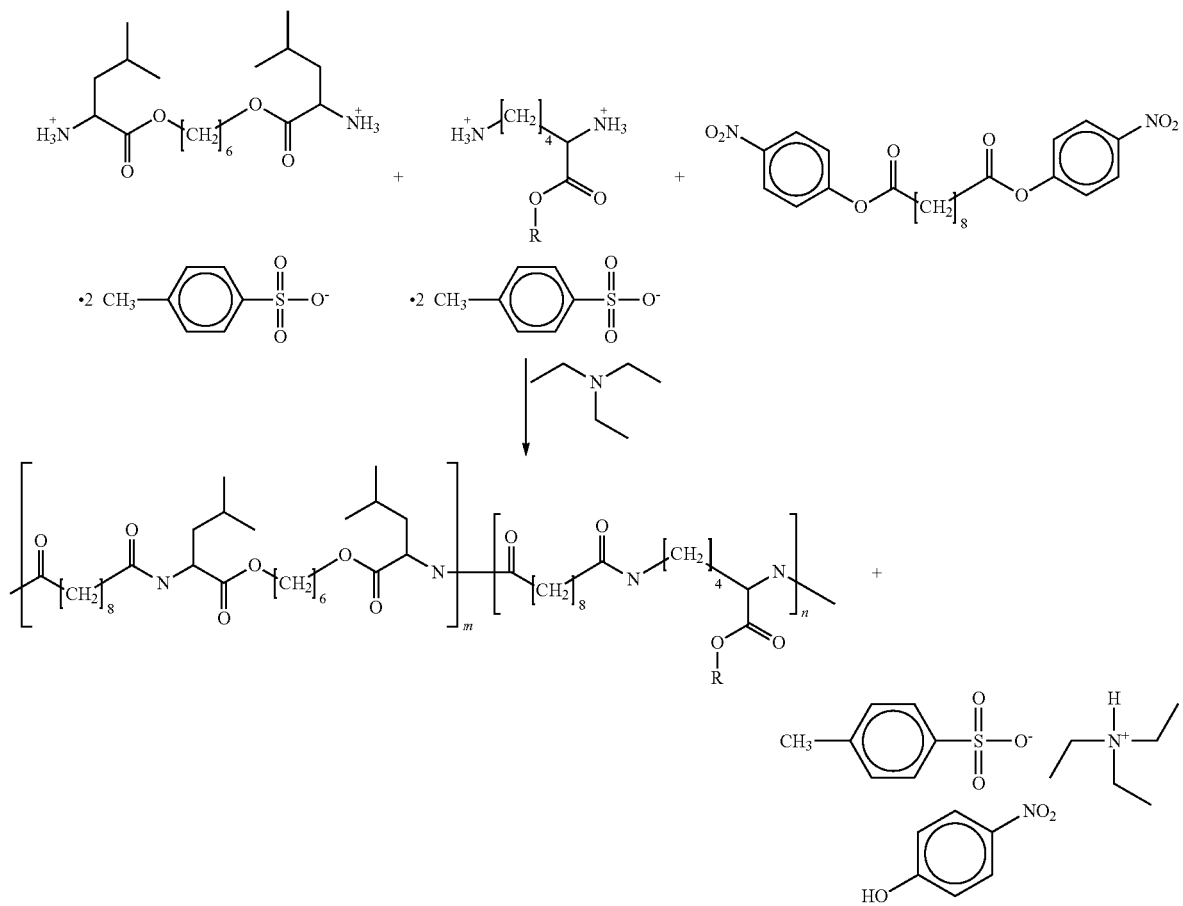

Referring to FIG. 1, three compositions of the coating composition system, labeled A, B and C, are subjected to a phase inversion process. The thermodynamics of the system can be chosen such that the initial compositions A, B and C follow the indicated mass transfer paths upon solvent evaporation so as to form three distinct PEA membrane morphologies. Composition A has a sufficiently small quantity of a drug and a non-solvent, such that the binodal curve is never crossed and the drug and polymer remain in a homogeneous mixture. Because the drug is miscible with the polymer and remains in the polymer matrix, the drug release kinetics is expected to be slower. However, as more drug (non-solvent) is added to the initial solution, the solution can become unstable upon solvent evaporation and can phase separate into a two-phase mixture. As more solvent evaporates, the PEA-rich phase can be driven into the glass transition region, thereby locking the varied morphologies and, thus, release-rate kinetics. For example, parameters such as solvent evaporation rate, solvent/non-solvent affinity, etc., can influence the phase inversion rate and thus will impact the final membrane structure. To illustrate, a solvent with a high evaporation rate (1) can cool the coating to induce a phase inversion, (2) can impart roughness or coarseness to the coating, and (3) can sometimes form channels or pores in the coating. The solvent/non-solvent affinity can affect the coating morphology in many ways. For example, if solvent and non-solvent are completely miscible, there will be rapid solvent exchange, leading to the formation of channels within the coating. If solvent and non-solvent are nearly immiscible, solvent exchange will be slow and a coating formed therefrom will have a dense and less porous morphology. If solvent and non-solvent have limited solubility (between the two extremes), then solvent exchange will be moderate and a coating formed therefrom will be porous. This phenomenon is linked to the phase inversion rate discussion below. As used herein, the term "porous" can refer to a coating having pores or channels. In some embodiments, the term "porous" can refer to a coating having solvent rich/polymer lean or non-solvent rich/polymer lean areas or regions.

Variation of coating polymers can also affect the dynamics of the phase inversion process. In general, fast phase inversion rates result in a large fraction of the two-phase system being in the non-solvent-rich phase. Additionally, this phase can be interconnected or take a form such as honeycomb structure, finger-type structure or the like. Such types of morphologies can exhibit faster drug release kinetics. Conversely, slower phase inversion rates can result in smaller fraction being non-solvent rich. In addition, the non-solvent rich phase may or may not be interconnected, resulting in phase structures ranging from dense structure with isolated, non-solvent pockets to honeycomb-type structures. Such types of morphologies will exhibit slower drug release kinetics.

In some embodiments, use of surfactant can be a formulation variable with which to control the size, shape, and gradient of the dispersed phase (i.e., the drug rich phase). The release rate of a drug can be a function of size distribution, shape, and gradient of the dispersed phase. Therefore, in some embodiments, a surfactant can be included in a coating composition system that would lower the interfacial tension during the phase inversion process and reduce the coarsening of the dispersed phase after the induction of the binodal decomposition. Any biocompatible surfactant, such as PLURONIC® (poly(ethylene oxide)-polypropylene oxide)-poly(ethylene oxide), TETRONIC® (tetra-functional block copolymers based on ethylene oxide and propylene oxide such as Polyol, available from BASF Corporation, Mount Olive, N.J.), Tween (Polysorbate surfactants), SPAN™ (Sorbitan based surfactant such as Sorbitan Monostearate), BRIJ® (Polyoxyethylene based surfactant such as polyoxyethylene (20) Oleyl ether), MYRJ™ (polyoxyethylene based surfactant such as Polyoxyethylene monostearate), SILWET™ (trisiloxane based surfactant), phospholipids, Poloxamer and combinations thereof, can be an exemplary surfactant that can be included in the coating composition system.

In some embodiments, a phase inversion process can be modulated by, for example, controlling the solvent evaporation rate in the phase inversion process so as to control the kinetics of the solid phase evolution in a coating. For example, the coating composition can additionally include an ingredient having a different boiling point from the solvent so as to increase or decrease the evaporation rate of the solvent. This ingredient can be a solvent or a non-solvent of a polymer in the coating composition.

According to the ternary phase diagram described above, an absorption-rate-controlled drug release can be a zero order release if, during the phase inversion process, the mass transfer line does not cross the binodal zone and the drug remains in the solid solution (see, FIG. 1). In this embodiment, the drug is soluble in the polymer matrix coating. Accordingly, in some embodiments, a phase inversion process as described herein can be used to form a coating having a drug release that is proportional to the absorption rate of the polymer matrix. As used herein, the term "zero order release" refers to a release profile where the release rate of a drug or agent remains unchanged or substantially unchanged over time after an onset release of the drug or agent. Similarly, a zero order absorption rate of a polymer refers to a rate of absorption of a polymer that remains unchanged or substantially unchanged over time.

In some embodiments, the phase conversion process described herein can be used to control mechanical properties of a coating. Mechanical properties are related to coating morphologies, the control of which is described above. For example, a coating having a dense morphology can be mechanically stronger than a coating having a large number of pores or channels.

Biocompatible Polymers

Any biocompatible polymer or polymeric material having a glass transition temperature greater than about ambient temperature can be used to form a coating composition that can be subjected to the phase inversion process described above in forming a coating on a medical device. The biocompatible polymer can be biodegradable (either bioerodable or bioabsorbable or both) or nondegradable, and can be hydrophilic or hydrophobic.

Representative biocompatible polymers include, but are not limited to, poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. poly(ethylene oxide-co-lactic acid) (PEO/PLA)), polyalkylene oxides such as poly(ethylene oxide), poly(propylene oxide), poly(ether ester), polyalkylene oxalates, phosphoryl choline, choline, poly(aspirin), polymers and co-polymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), Pluronic™ surfactants (polypropylene oxide-co-polyethylene glycol), poly (tetramethylene glycol), hydroxy functional poly(vinyl pyrrolidone), biomolecules such as collagen, chitosan, alginate, fibrin, fibrinogen, cellulose, starch, dextran, dextrin, hyaluronic acid, fragments and derivatives of hyaluronic acid, heparin, fragments and derivatives of heparin, glycosamino glycan (GAG), GAG derivatives, polysaccharide, elastin, or combinations thereof. In some embodiments, the coatings can exclude any one of the aforementioned polymers.

As used herein, the terms poly(D,L-lactide), poly(L-lactide), poly(D,L-lactide-co-glycolide), and poly(L-lactide-co-glycolide) can be used interchangeably with the terms poly (D,L-lactic acid), poly(L-lactic acid), poly(D,L-lactic acid-co-glycolic acid), or poly(L-lactic acid-co-glycolic acid), respectively.

Biobeneficial Material

In some embodiments, the biocompatible polymer or polymeric material described above can include a biobeneficial material. The biobeneficial material can be a polymeric material or non-polymeric material. The biobeneficial material is preferably non-toxic, non-antigenic and non-immunogenic. A biobeneficial material is one which enhances the biocompatibility of the coating or device by being non-fouling, hemocompatible, actively non-thrombogenic, or anti-inflammatory, all without depending on the release of a pharmaceutically active agent.

Representative biobeneficial materials include, but are not limited to, polyethers such as poly(ethylene glycol), copoly (ether-esters) (e.g. PEO/PLA), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly (ethylene glycol) acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), Pluronic™ surfactants (polypropylene oxide-co-polyethylene glycol), poly(tetramethylene glycol), hydroxy functional poly(vinyl pyrrolidone), biomolecules such as fibrin, fibrinogen, cellulose, starch, collagen, dextran, dextrin, hyaluronic acid, fragments and derivatives of hyaluronic acid, heparin, fragments and derivatives of heparin, glycosamino glycan (GAG), GAG derivatives, polysaccharide, elastin, chitosan, alginate, silicones, POLYACTIVE™, and combinations thereof. In some embodiments, the coatings can exclude any one of the aforementioned polymers.

The term PolyActive™ refers to a block copolymer having flexible poly(ethylene glycol) and poly(butylene terephthalate) blocks (PEGT/PBT). PolyActive™ is intended to include AB, ABA, BAB copolymers having such segments of PEG and PBT (e.g., poly(ethylene glycol)-block-poly(butyleneterephthalate)-block poly(ethylene glycol) (PEG-PBT-PEG).

In a preferred embodiment, the biobeneficial material can be a polyether such as poly (ethylene glycol) (PEG) or polyalkylene oxide.

Bioactive Agents

A coating composition system that can be subjected to the phase inversion described above can include any bioactive agent. The bioactive agent can be any bioactive agent, which is a therapeutic, prophylactic, or diagnostic agent. These agents can have anti-proliferative or anti-inflammatory properties or can have other properties such as antineoplastic, antiplatelet, anti-coagulant, anti-fibrin, antithrombotic, antimitotic, antibiotic, antiallergic, and antioxidant. The agents can be cytostatic agents, agents that promote the healing of the endothelium such as NO releasing or generating agents, agents that attract endothelial progenitor cells, or agents that promote the attachment, migration and proliferation of endothelial cells (e.g., natriuretic peptide such as CNP, ANP or BNP peptide or an RGD or cRGD peptide), while quenching smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Some other examples of the bioactive agent include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy) ethyl-rapamycin (everolimus), and its functional or structural derivatives, paclitaxel and its functional and structural derivatives. Examples of rapamycin derivatives include 40-epi-(N1-tetrazolyl)-rapamycin (ABT-578), 40-O-(3-hydroxy) propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax™ (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, or combinations thereof. Examples of cytostatic substances include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, bioactive RGD, and genetically engineered endothelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient, the nature of the trauma, the nature of the therapy desired, the time over which the ingredient administered resides at the vascular site, and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of Implantable Device

As used herein, an implantable device may be any suitable medical substrate that can be implanted in a human or veterinary patient. Examples of such implantable devices include self-expandable stents, balloon-expandable stents, stent-grafts, grafts (e.g., aortic grafts), heart valve prostheses, cerebrospinal fluid shunts, pacemaker electrodes, catheters, endocardial leads (e.g., FINELINE® and ENDOTAK®, available from Guidant Corporation, Santa Clara, Calif.), anastomotic devices (e.g., CABG anastomotic clips) and connectors, orthopedic implants such as screws, spinal implants, and electro-stimulatory devices. The underlying structure of the device can be of virtually any design. The device can be made of a metallic material or an alloy such as, but not limited to, cobalt chromium alloy (ELGILOY®), stainless steel (316L), high nitrogen stainless steel, e.g., BIODUR® 108, cobalt chrome alloy L-605, "MP35N," "MP20N," ELASTINITE® (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. In some embodiments, the device is an absorbable stent.

Method of Use

In accordance with embodiments of the invention, a coating subjected to the treatment of a phase inversion process described above can be used to provided controlled release of a bioactive agent from a medical device (e.g., stent) during delivery and (in the case of a stent) expansion of the device, or thereafter, at a desired rate and for a predetermined time at the implantation site.

Preferably, the medical device is a stent. The stent described herein is useful for a variety of medical procedures, including, for example, treatment of obstructions caused by tumors in bile ducts, esophagus, trachea/bronchi and other biological passageways. A stent having the above-described coating is particularly useful for treating diseased regions of blood vessels caused by lipid deposition, monocyte or macrophage infiltration, or dysfunctional endothelium or a combination thereof, or occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, carotid and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter that allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described features may then be expanded at the desired area of treatment. A post-insertion angiogram may also be utilized to confirm appropriate positioning.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:
1. An implantable device comprising a coating comprising a bioactive agent and a poly(ester amide) polymer, the poly (ester amide) polymer formed from L-leucine, cyclohexanediol, straight chain hexanediol, and sebacic acid.
2. The implantable device of claim 1, which is a stent.
3. The implantable device of claim 1, wherein the poly (ester amide) polymer is of the formula:

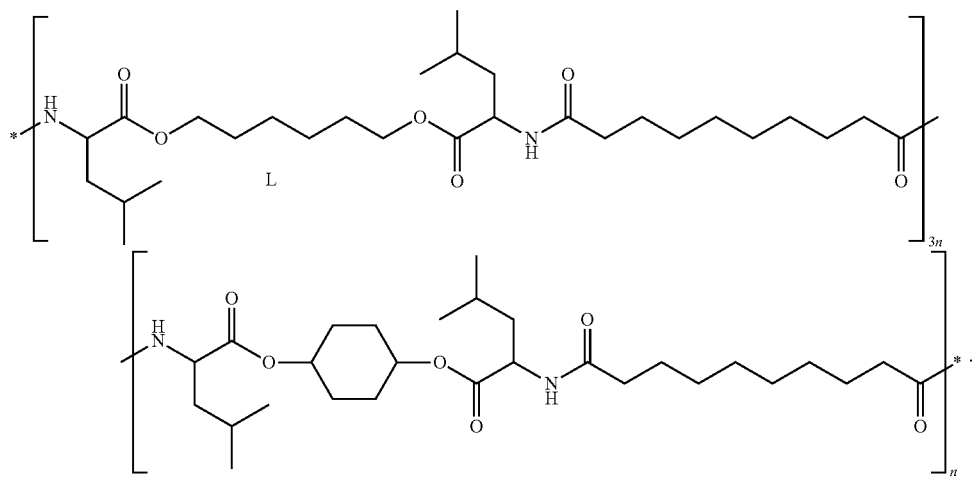

4. The implantable device of claim 1, wherein the bioactive agent is selected from the group consisting of rapamycin, everolimus, 40-epi-(N1-tetrazolyl)-rapamycin (ABT-578), 40-O-(3-hydroxy)propyl-rapamycin, 40-O-[2-(2-hydroxy)ethoxy]ethyl-rapamycin, 40-O-tetrazole-rapamycin, docetaxel, paclitaxel, and combinations thereof.

5. The implantable device of claim 3, wherein the bioactive agent is selected from the group consisting of rapamycin, everolimus, 40-epi-(N1-tetrazolyl)-rapamycin (ABT-578), 40-O-(3-hydroxy)propyl-rapamycin, 40-O-[2-(2-hydroxy)ethoxy]ethyl-rapamycin, 40-O-tetrazole-rapamycin, docetaxel, paclitaxel, and combinations thereof.

6. The implantable device of claim 4, wherein the bioactive agent is everolimus, 40-epi-(N1-tetrazolyl)-rapamycin (ABT-578), or a combination thereof.

7. The implantable device of claim 5, wherein the bioactive agent is everolimus, 40-epi-(N1-tetrazolyl)-rapamycin (ABT-578), or a combination thereof.

* * * * *